(12) United States Patent  (10) Patent No.: US 9,241,857 B2
Cox  (45) Date of Patent: Jan. 26, 2016

(54) ACCESSORY BAR FOR A TREATMENT BED

(71) Applicant: Larry E. Cox, Charlevoix, MI (US)

(72) Inventor: Larry E. Cox, Charlevoix, MI (US)

( * ) Notice: Subject to any disclaimer, the term of this patent is extended or adjusted under 35 U.S.C. 154(b) by 0 days.

(21) Appl. No.: 14/789,147

(22) Filed: Jul. 1, 2015

(65) Prior Publication Data

US 2015/0313781 A1  Nov. 5, 2015

Related U.S. Application Data

(63) Continuation-in-part of application No. 13/505,135, filed as application No. PCT/US2009/062690 on Oct. 30, 2009, now abandoned.

(51) Int. Cl.
*A61G 7/05* (2006.01)
*A61G 13/10* (2006.01)
*A61F 7/00* (2006.01)

(52) U.S. Cl.
CPC ............... *A61G 7/0503* (2013.01); *A61F 7/00* (2013.01); *A61G 7/05* (2013.01); *A61G 13/10* (2013.01)

(58) Field of Classification Search
CPC ........................................................ A61G 7/05
USPC .................................. 5/658, 652, 421, 503.1
See application file for complete search history.

(56) References Cited

U.S. PATENT DOCUMENTS

| 4,557,453 | A  | * | 12/1985 | McCloskey | A61G 7/05 248/283.1 |
| 6,486,792 | B1 | * | 11/2002 | Moster | A47C 31/008 297/411.2 |
| 7,043,306 | B2 | * | 5/2006 | Park | A61H 7/001 601/94 |
| 8,011,629 | B2 | * | 9/2011 | Herskovic | A61G 7/0503 248/229.13 |

* cited by examiner

*Primary Examiner* — Fredrick Conley
(74) *Attorney, Agent, or Firm* — Dinsmore & Shohl LLP; Allen M. Krass

(57) ABSTRACT

An accessory bar for a treatment bed is disclosed. The bar comprises a bracket releasably mounted, in use, to said treatment bed. An upright extends upwardly from the bracket in use. In one embodiment, an arm extends transversely from the upright. The arm has extending therefrom one or more pairs of posts. The posts extend generally horizontally, towards the area over the bed, in use.

5 Claims, 23 Drawing Sheets

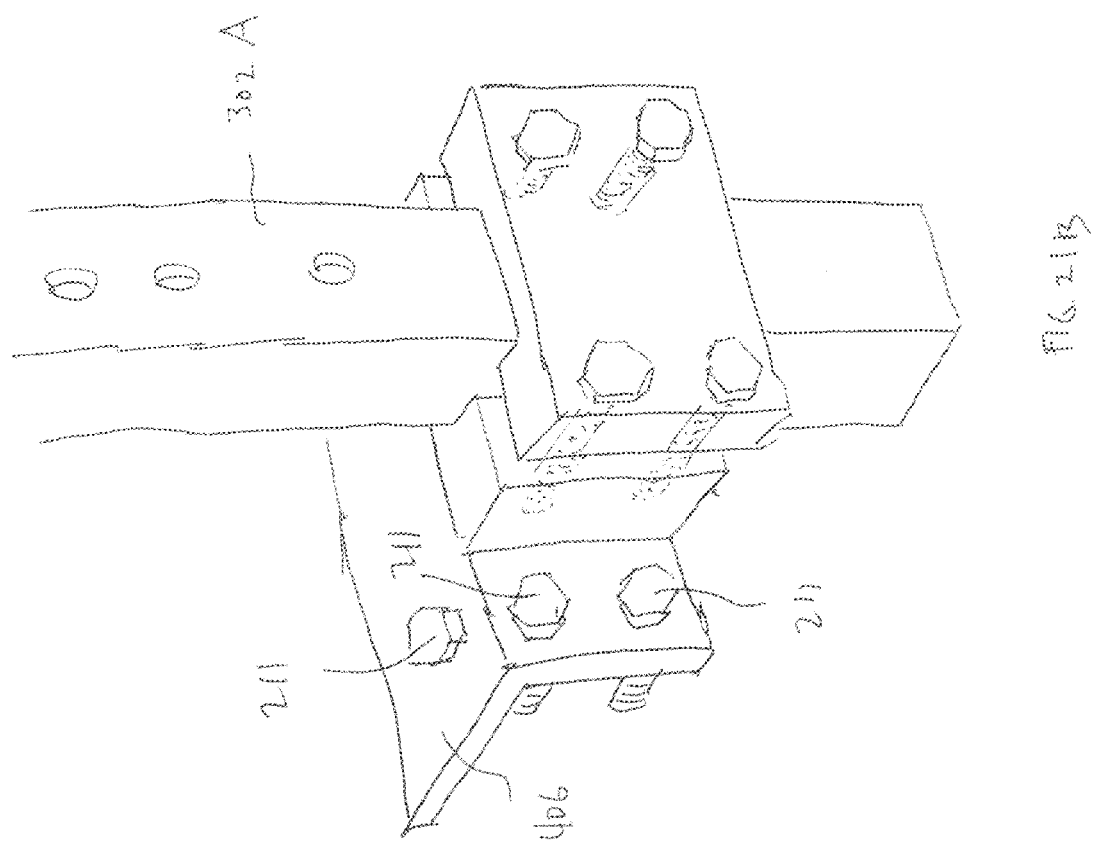

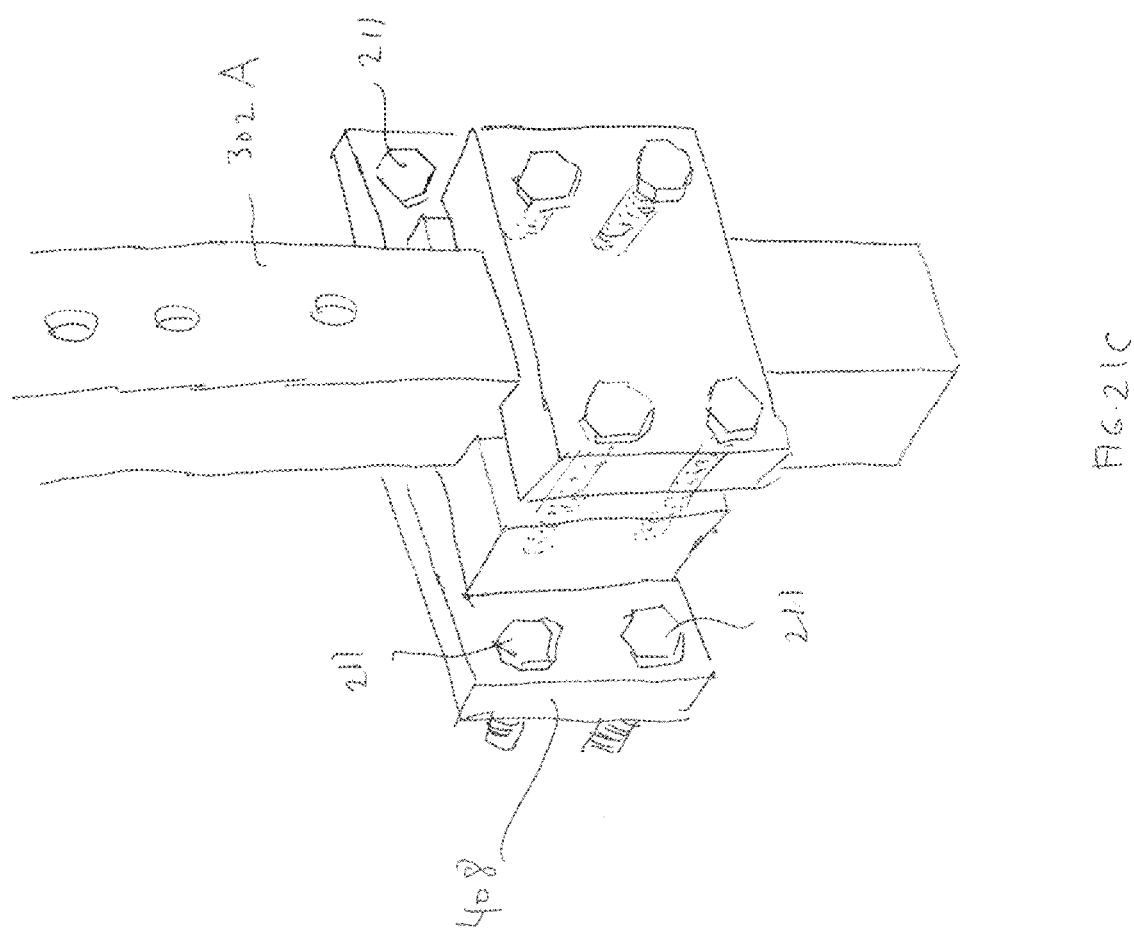

ACCESSORY BAR FOR A TREATMENT BED

CROSS-REFERENCE TO RELATED APPLICATIONS

This application is a continuation-in-part of U.S. patent application Ser. No. 13/505,135 filed Apr. 30, 2012, which is the U.S. National Phase of PCT/US2009/062690 filed Oct. 30, 2009.

FIELD OF THE INVENTION

The present invention relates to the field of personal wellness.

BACKGROUND OF THE INVENTION

Thermal (infrared) massage, as a tool to enhance personal wellness and immune function, is gaining consumer acceptance worldwide. As a result of this increased awareness and acceptance, a plurality of specialized tools are reaching the marketplace. One type of tool that has reached the marketplace is a treatment system which includes a treatment bed, first and second treatment appliances, a treatment mat and first and second remote control units. The treatment bed has a main body pad, a lower body pad, a bed frame and a pair of grips. The main body pad is for supporting and selectively applying heat and massage to the main (upper) body of a user in the supine or prone position. The lower body pad is for supporting and selectively applying heat and massage to the lower body of the user. The bed frame is for supporting the main body pad and the lower body pad in use. The grips are bolted on opposite sides of the frame and are for assisting the user in movement to and from the supine and prone positions on the treatment bed. The first and second treatment appliances are for placement against a selected body region and selectively applying heat and point pressure thereto. Each appliance includes a waisted portion and the second appliance is larger than the first. The treatment mat has a hand-grip and is for producing far infrared radiation and negative ions. The first remote control unit is for controlling the first and second treatment appliances and the main and lower body pads. The second remote control unit is for controlling the mat and has a socket defined therein.

SUMMARY OF THE INVENTION

Forming one aspect of the invention is, in combination: (1) an energetic medical device having a waisted portion; (2) a treatment bed having one or more cushions for supporting a user in the supine or prone position and a bed frame supporting the one or more cushions; and (3) a support frame: bolted to the bed frame; and including a pair of horizontally extending posts adapted to receive therebetween the waisted portion of said energetic medical device to support the energetic medical device in elevated relation above and to one side of the treatment bed.

Forming another aspect of the invention a system for use with: (1) a treatment bed having: one or more cushions for supporting a user in the supine or prone position; a bed frame supporting the one or more cushions; and a pair of grips, bolted on opposite sides of the bed frame, for assisting the user in movement to and from the supine and prone positions; and (2) an energetic medical device having a waisted portion. This system comprises: a support frame adapted to be bolted to the frame to define an upright disposed to one side of the treatment bed, the upright having a plurality of bores defined therein; a lateral having a plurality of bores defined therein, at least a pair of the bores being spaced apart the width of the waisted portion; a cruciform bracket adapted to couple the lateral to the upright in use such that the bores present towards the treatment bed; posts engageable in the pair of bores such that, when the frame, lateral, cruciform bracket and posts are operatively assemble, the posts are adapted to support the energetic medical device in elevated relation above and to one side of the treatment bed.

According to another aspect of the invention, the system can comprise a hook adapted to be secured to the lateral to support a treatment mat.

According to another aspect of the invention, the system can comprise a mounting block adapted to be secured to any of the bores of the upright or the lateral.

According to another aspect of the invention: the support frame can be adapted to be secured to the bed frame in use such that one or more of the bolts bolting the support frame to the bed frame can form part of the bolts by which the grips are mounted to the bed frame; and the system can further comprise a mounting bracket adapted to be secured to the bed frame and to support the upright without use of the bolts by which the grips are mounted to the bed frame.

Other advantages, features and characteristics of the present invention, as well as methods of operation and functions of the related elements of the structure, and the combination of parts and economies of manufacture, will become more apparent upon consideration of the following detailed description and the appended claims with reference to the accompanying drawings, the latter being briefly described hereinafter.

BRIEF DESCRIPTION OF THE DRAWINGS

FIG. 21B is a view of another embodiment of a portion of the structure of FIG. 19; and FIG. 21C is a view of another embodiment of the structure of FIG. 21B.

DETAILED DESCRIPTION OF THE PREFERRED EMBODIMENTS

Figure 1:
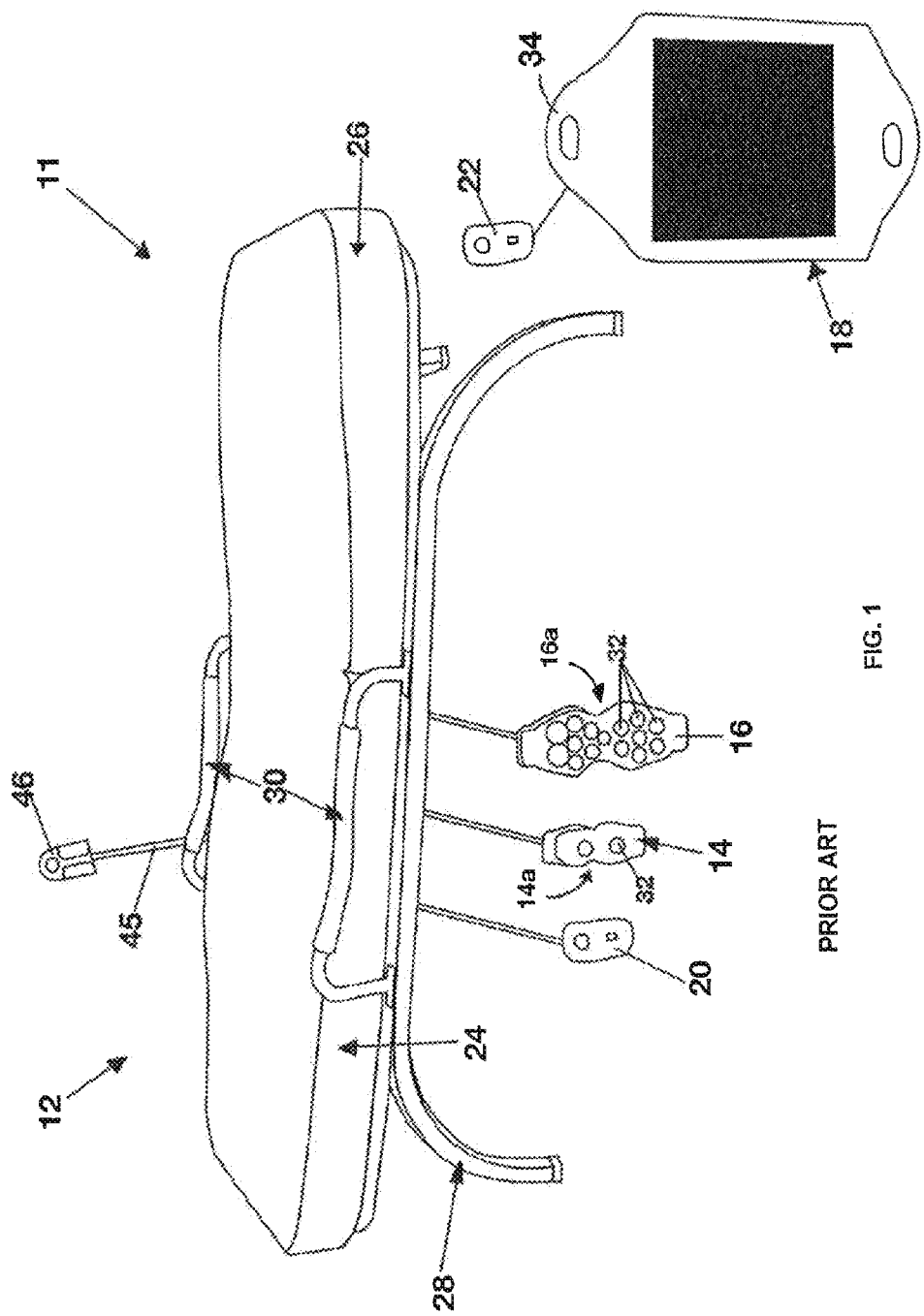
FIG. 1 shows a prior art treatment system.

The present invention relates to the field of wellness and, in an exemplary embodiment, relates to a treatment system. For clarity in the description of the invention, a prior art treatment system 11, with which the invention can be used but which forms no part of the invention, will firstly be described with reference to FIG. 1

The treatment system 11 is of the type including a treatment bed 12, first 14 and second 16 treatment appliances, a treatment mat 18 and first 20 and second 22 remote control units.

The treatment bed 12, first 14 and second 16 treatment appliances and first remote control unit 14 are sold by Migun Medical Instrument Co. under Model No. HY-7000 UM.

The treatment mat 18 and the second remote control unit 22 are sold by Migun Medical Instrument Co. under Model No. MG-3600.

The treatment bed 12 has a main body cushion 24, a lower body cushion 26, a bed frame 28, a pair of grips 30 and a cradle 46.

The main body cushion 24 is for supporting and selectively applying heat and massage to upper body of a user in the supine or prone position on the treatment bed. The lower body cushion 26 is for supporting and selectively applying heat and massage to the lower body of the user. For the purpose of applying heat and massage, each of the main body 24 and lower body 26 cushions includes devices for producing far infrared radiation, and well as vibrators.

The bed frame 28 is for supporting the main body cushion 24 and the lower body cushion 26 in use and is formed out of tubular elements, bolted together.

The grips 30 are bolted on opposite sides of the frame 28 and are for assisting the user in movement to and from the supine and prone positions on the bed 12.

The first 14 and second 16 treatment appliances are for placement against a selected body region and selectively applying heat and point pressure thereto. Each appliance includes a waisted portion 14A, 16A and the second appliance 16 is larger than the first appliance 14. For the purpose of applying heat each of these appliances 14,16 includes a device for producing far infrared radiation.

For the purpose of applying point pressure, each of these devices includes hard surfaces, specifically, jade stones 32. The first device 14 includes two stones 32, and the second device 16 includes 15 stones.

The cradle 46 is releasably mounted to the frame 28 via an intermediate flexible shaft 45 having a threaded bore at its end (not shown) and releasably receives the first remote control unit 20, discussed below, when not in use. To releasably mount the cradle 46 to the frame 28, a bolt (not shown) passes through a bore (not shown) in the frame 28 and threads into the threaded bore at the end of shaft 45, to secure the shaft 45 to the frame 28.

The treatment mat 18 has a hand-grip 34 and is adapted to produce far infrared radiation, for heating purposes, as well as negative ions.

The first remote control unit 20 is for controlling the first 14 and second 16 treatment appliances and the main 24 and lower 26 body cushions.

Figure 11:
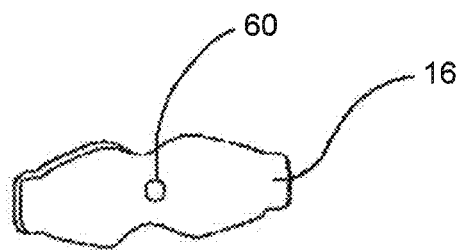
FIG. 11 is a rear view of a second appliance of the prior art treatment system of FIG. 1.

The second remote control unit 22 is for controlling the treatment mat 18 and has a socket 60 defined therein, as shown in FIG. 11.

Figure 2:
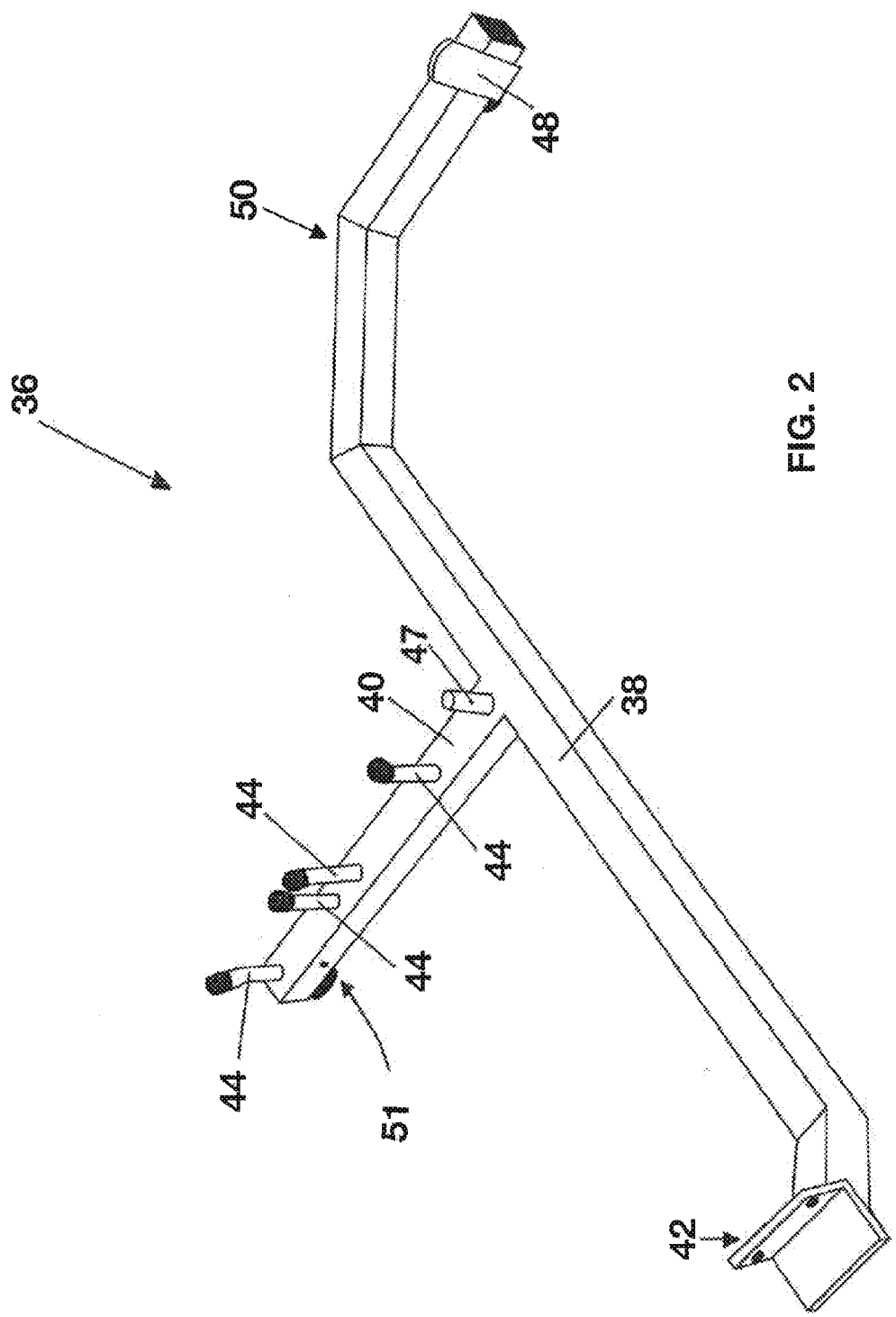
FIG. 2 shows apparatus according to an exemplary embodiment of the present invention.

Turning now to the apparatus of the present invention, same will be seen in isolation in FIG. 2 and will be seen to comprise a support frame 36 which includes an upright 38, an arm 40, a bracket 42, posts 44, pin 47 and a hook 48. The upright 38 forms part of a crook 50. The arm 40 extends transversely from the upright 38 and has pin 47 extending therefrom and a bore 51 defined therethrough. Bracket 42 is rigidly connected, by welding, to the base of the upright 38. Two pairs of posts 44 are provided, which protrude from the arm 40. The hook 48 defines the terminus of the crook 50. The crook 50, the upright 38 and the arm 40 are substantially coplanar, with the hook 48 and the arm 40 lying on opposite sides of the upright 38. At the base of the upright 38, immediately preceding the bracket 42, the upright 38 jogs slightly.

Figure 3:
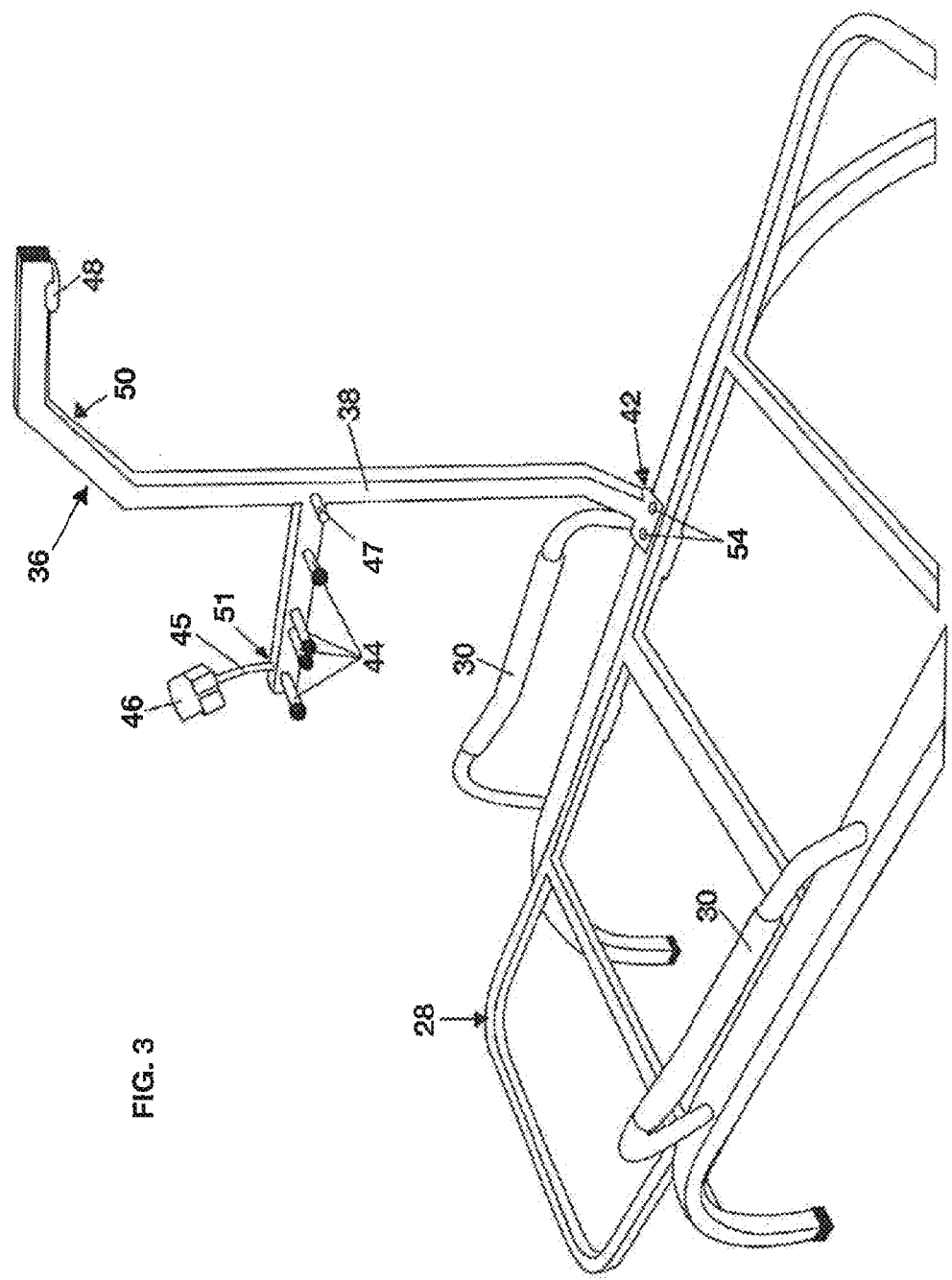
FIG. 3 shows the apparatus of FIG. 2 in use with part of the structure of FIG. 1.
Figure 4:
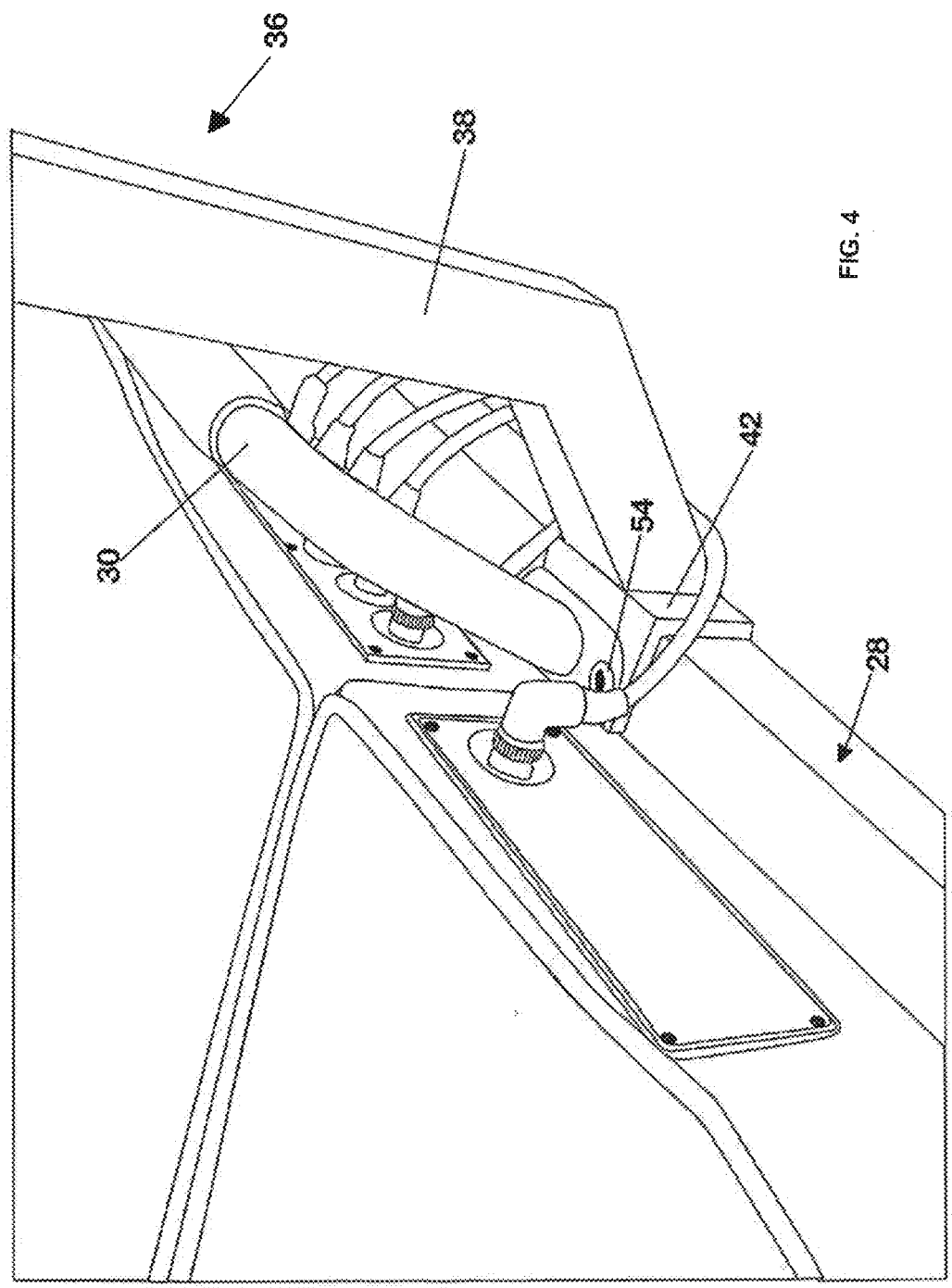
FIG. 4 is a partial view of the apparatus of FIG. 2 in use with another part of the structure of FIG. 1.

For use, the support frame 36 is releasably secured, specifically, by bolts 54, to the bed frame 28 in use, as shown in FIG. 3 and FIG. 4. More particularly, the support frame 36 is bolted to the bed frame 28 in use using the same bores as used to secure one of the grips 30, i.e. one or more of the bolts 54 bolting the support frame 36 to the bed frame 28 form part of the bolts by which the grips 30 are mounted to the bed frame 28. The bolt holding the flexible shaft 45 of the cradle 46 is also removed from the bed frame 28, to release shaft 45, and the bolt is fitted through bore 51 of the support frame, and thence back into the threaded bore in the shaft 45, to secure the shaft/cradle to the support frame.

Figure 5:
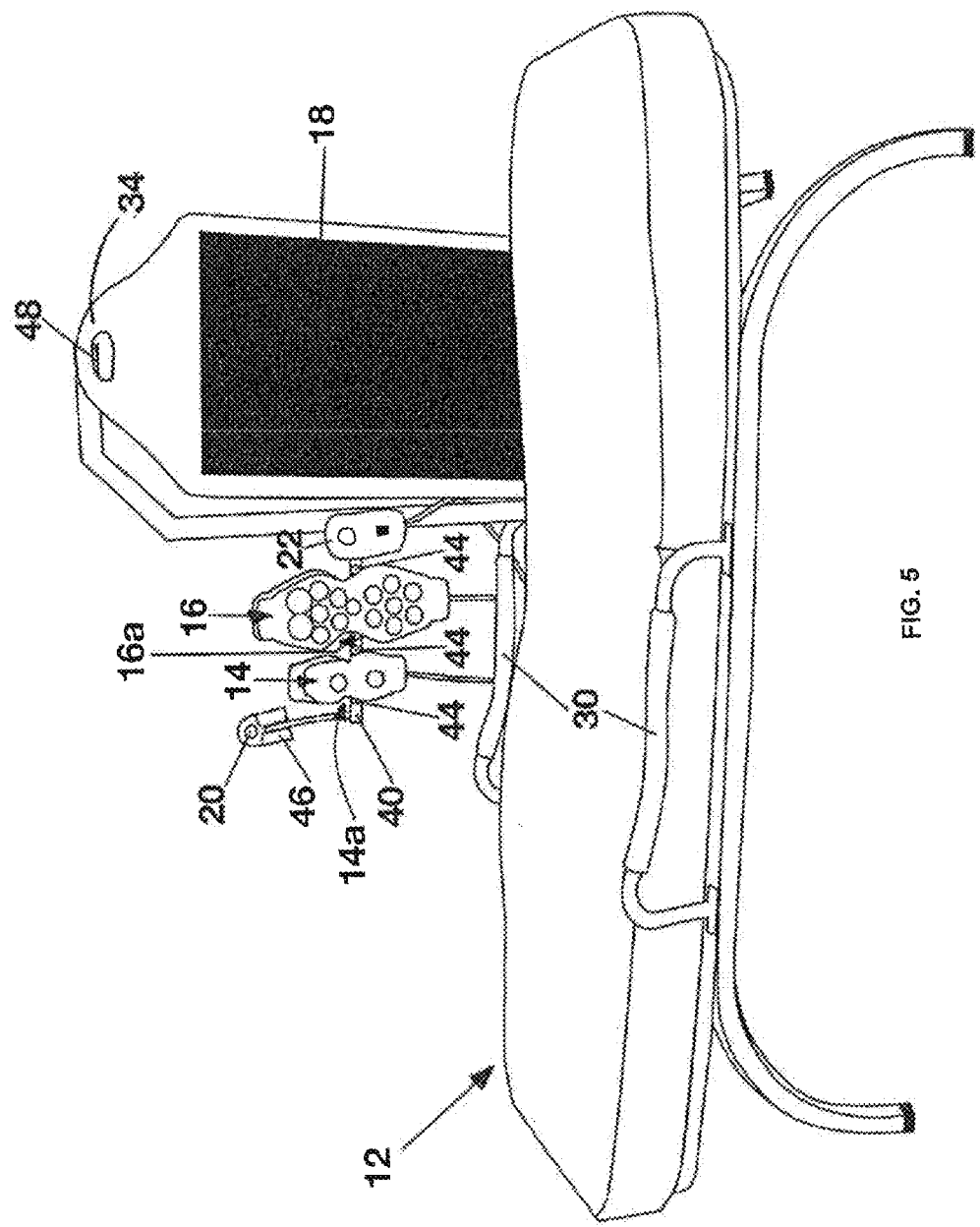
FIG. 5 is a view of the apparatus of FIG. 2 in use with the structure of FIG. 1.

The apparatus is shown in use in FIG. 5. Herein, it will be seen that the apparatus is adapted to releasably receive and supporting in elevated relation, above and to one side of the treatment bed 12, each of the first 14 and second treatment 16 appliances, the treatment mat 18 and the first 20 and second 22 remote control units. More particularly, the waisted portions 14A, 16A of each appliance 14,16 are releasably received between a respective pair of posts 44, the cradle 46 is in releasably receipt of the first remote control 20; the pin (not visible in FIG. 5) is in releasable receipt of the socket of the second remote control unit 22 and the hook 48 is in releasable receipt of the hand-grip 34 of the mat 18.

The apparatus will thus be seen to conveniently store all of the accessories associated with the treatment system, and thus is aptly described as an 'accessory bar'. The accessory bar avoids damage/injury that might otherwise occur if the appliances/remote controls were simply left between use on the bed itself or the surrounding floor surface. As well, the bar keeps the appliances/controls in a location convenient for self-users, who might otherwise be required to lift them from the floor while on the bed, or hold onto them while mounting and dismounting the bed, adding to the potential for injury. The 'jog' in the upright, previously mentioned, ensures that the accessory bar and the accessories themselves, are disposed slightly to the side of the table, about 3" from the edge of the cushions, so as not to interfere with ingress/egress.

Variations of this are, of course, possible.

Figure 6:
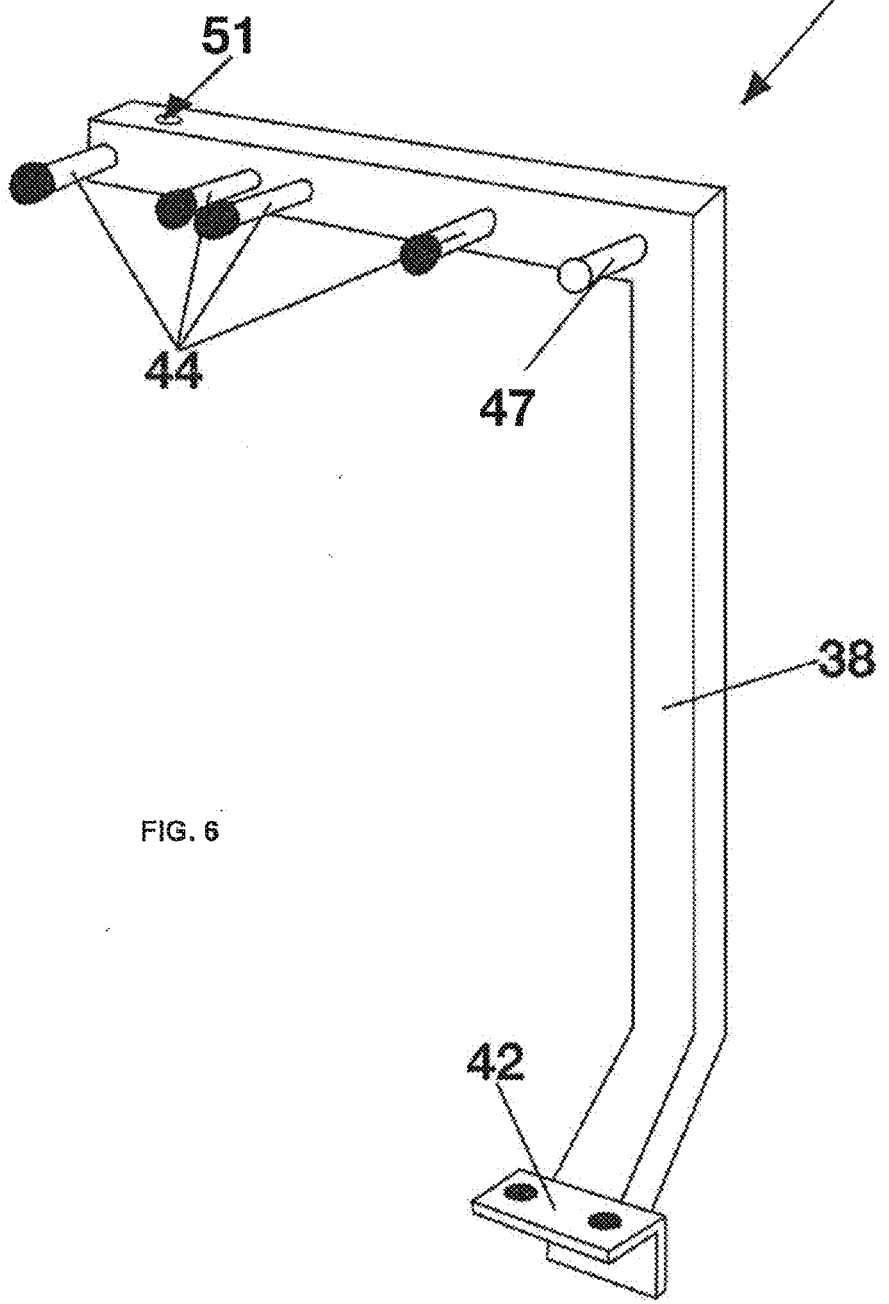
FIG. 6 is a view of apparatus according to another exemplary embodiment of the present invention.

FIG. 6, for example, shows a variation 36A which does not include the hook/crook. This could be advantageous, as not all users will have use for and purchase the treatment mat.

Figure 7:
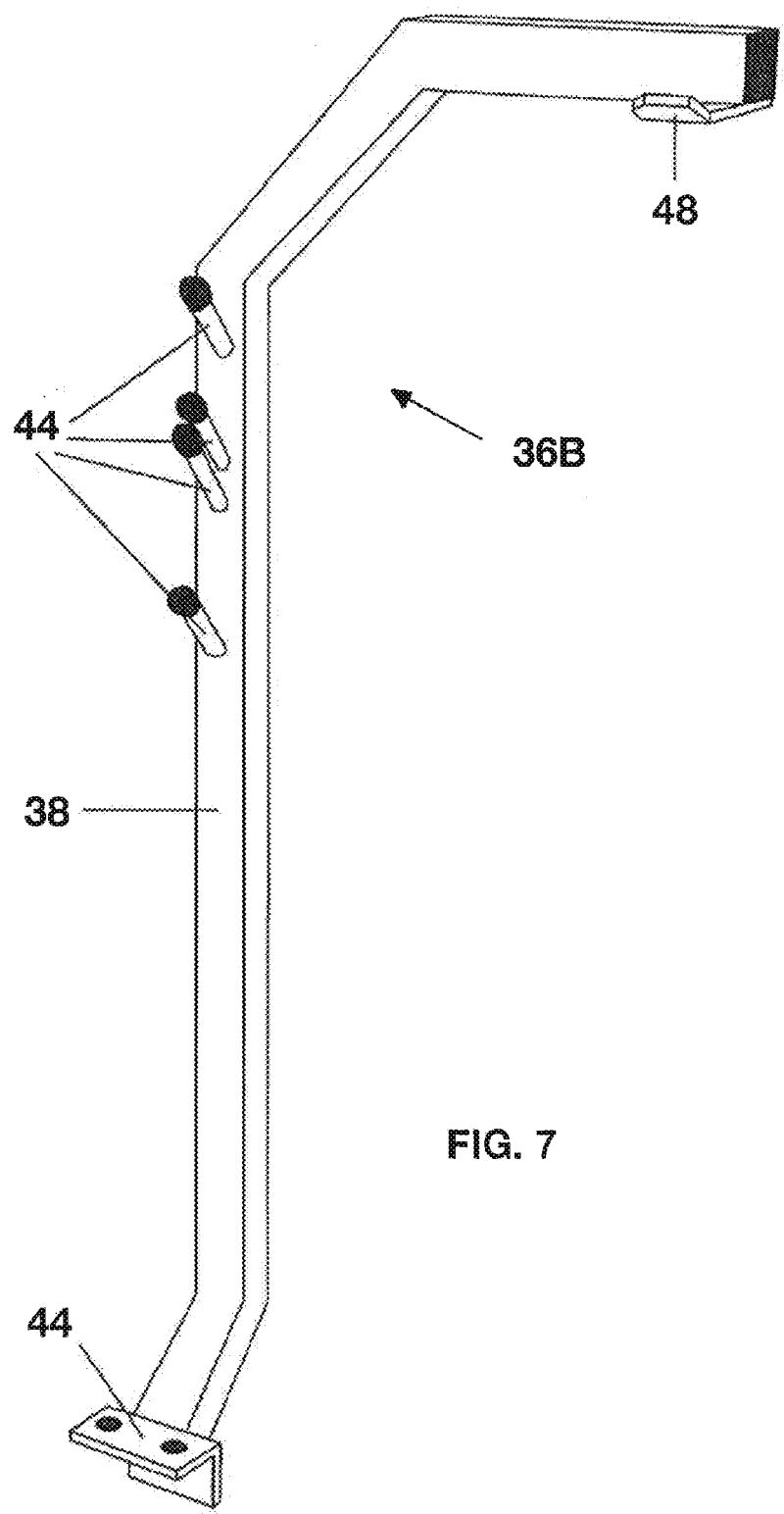
FIG. 7 is a view of apparatus according to yet another exemplary embodiment of the present invention.

FIG. 7 shows another example 36B, wherein the posts protrude from the upright, i.e. with no transverse arm.

Figure 8:
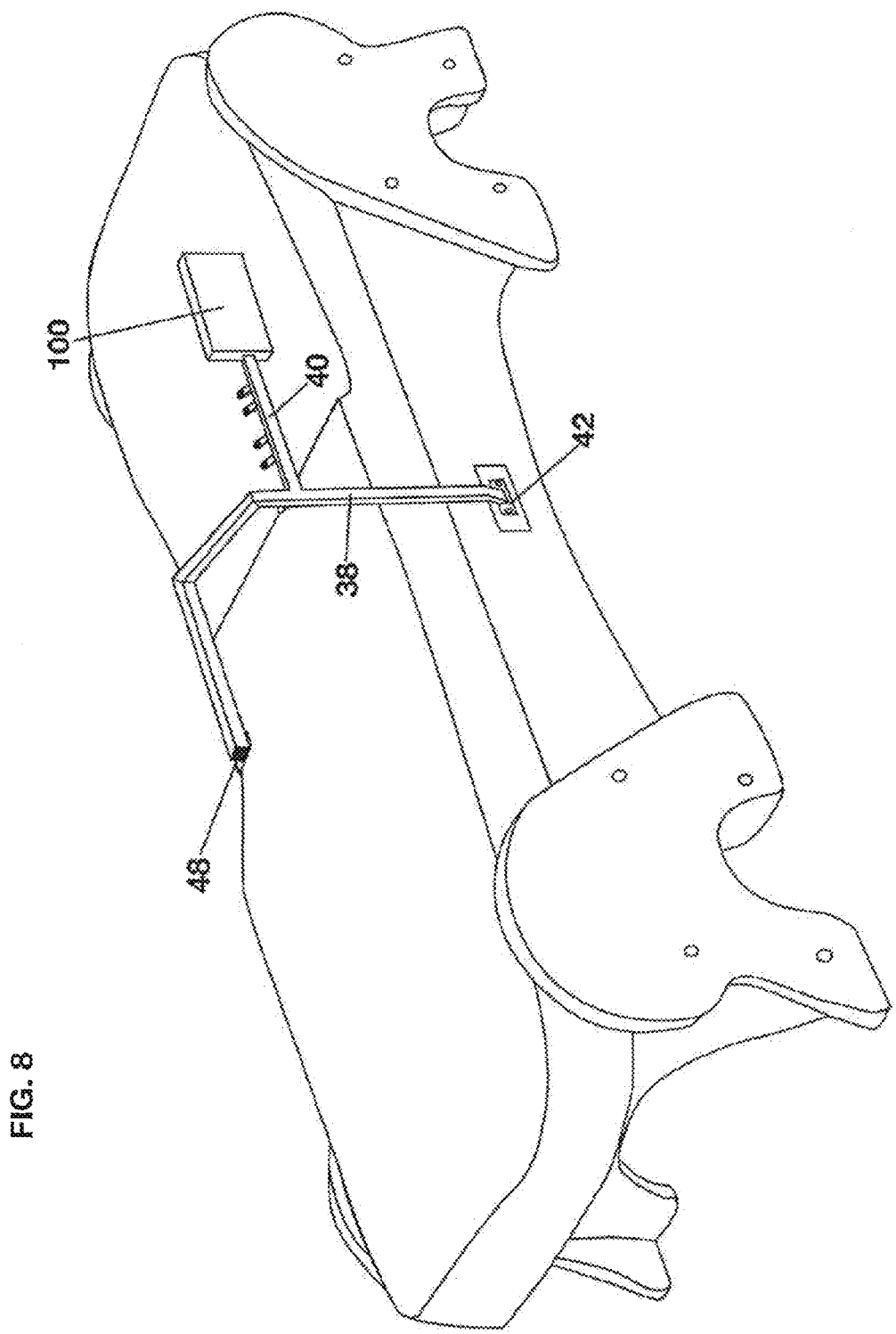
FIG. 8 is a view of apparatus according to yet another exemplary embodiment of the present invention in use.

As well, whereas a specific model of treatment bed is illustrated and referenced, it will be understood that the support frame could be utilized with beds of other manufacturers and other styles. FIG. 8, for example, shows a variant of the mounting bracket mounted to a treatment bed of the type formed out of wood panels. Depending upon the treatment bed with which the support frame is used, suitable accommodation will need to be made, inter alia, to the jog in the upright, to provide sufficient clearance to users, as will be evident to persons of ordinary skill in the art.

Figure 9:
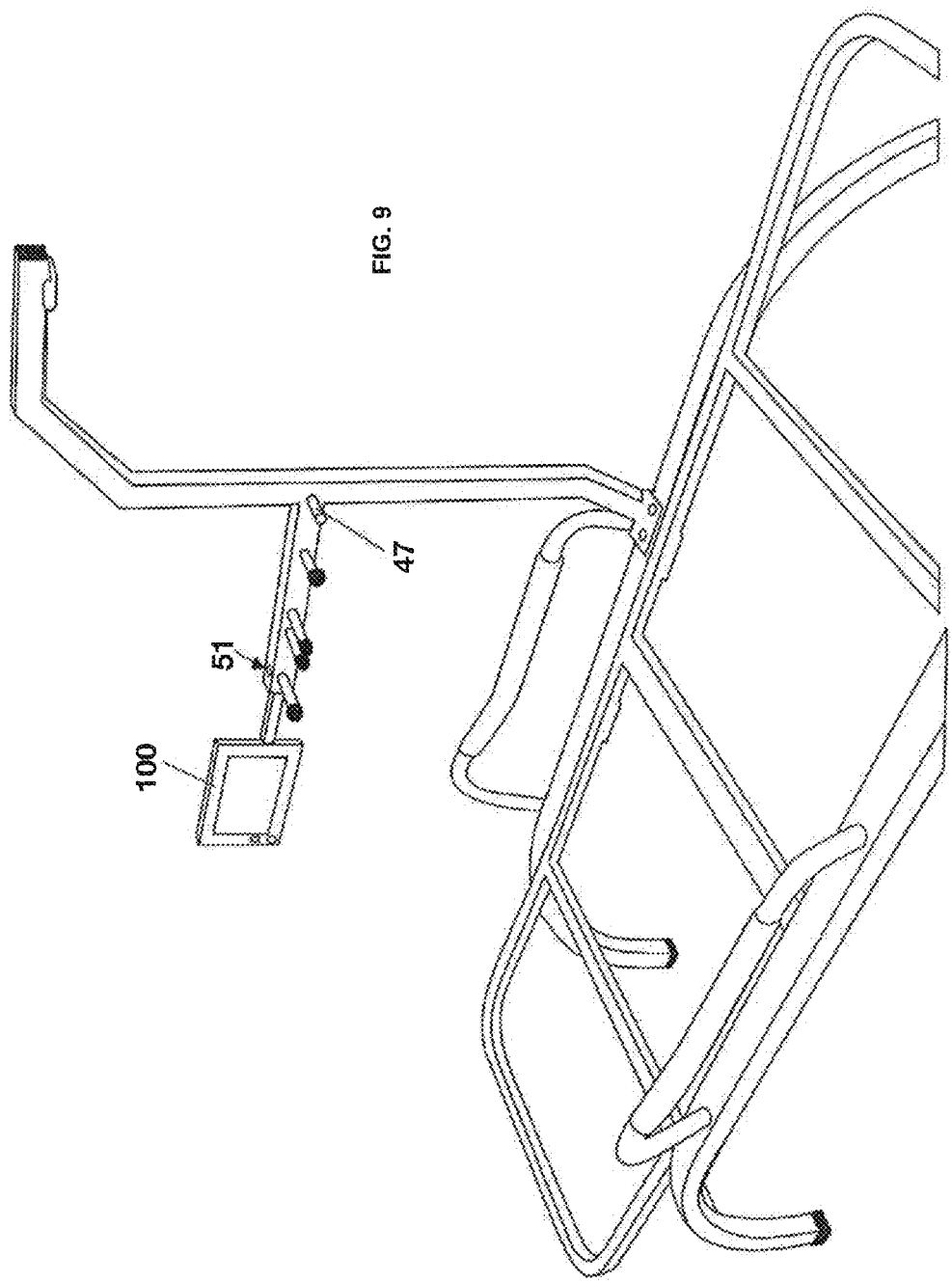
FIG. 9 is a view similar to FIG. 3 but showing apparatus according to yet another exemplary embodiment of the present invention.

The support frame could also be adapted to receive a video monitor 100, as shown in FIG. 9. The monitor 100, which becomes easily viewable when mounted on the support frame, could be used advantageously for marketing and instructional purposes.

Figure 10:
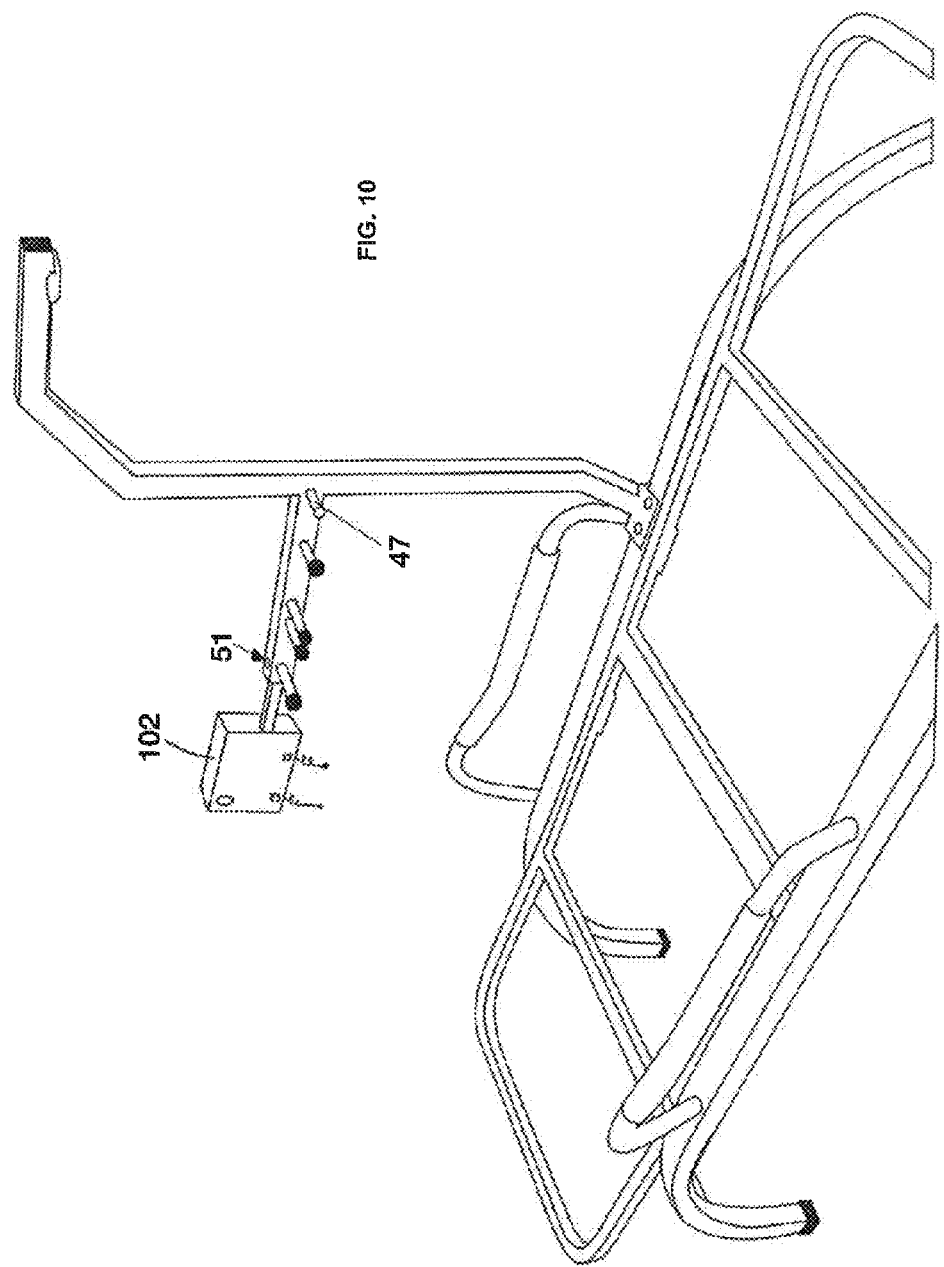
FIG. 10 is a view similar to FIG. 3 but showing apparatus according to yet another exemplary embodiment of the present invention.

As well, whereas specific treatment appliances and mats are herein shown and described, it will be understood that the invention could readily be used with other energetic medical devices and diagnostic devices, either as substitutes for, or supplemental to, those illustrated and described herein. FIG. 10, for example, shows the accessory bar in use with a diagnostic device 102.

Further, although not shown, the bar could be made telescopic, for greater flexibility.

Also not shown, a credit card reader could be provided and received, for example, in a manner analogous to the manner in which the video monitor is mounted. This would, for example, allow the treatment system to be installed on a pay-per-use basis in airports, hotels, etc.

Figure 12:
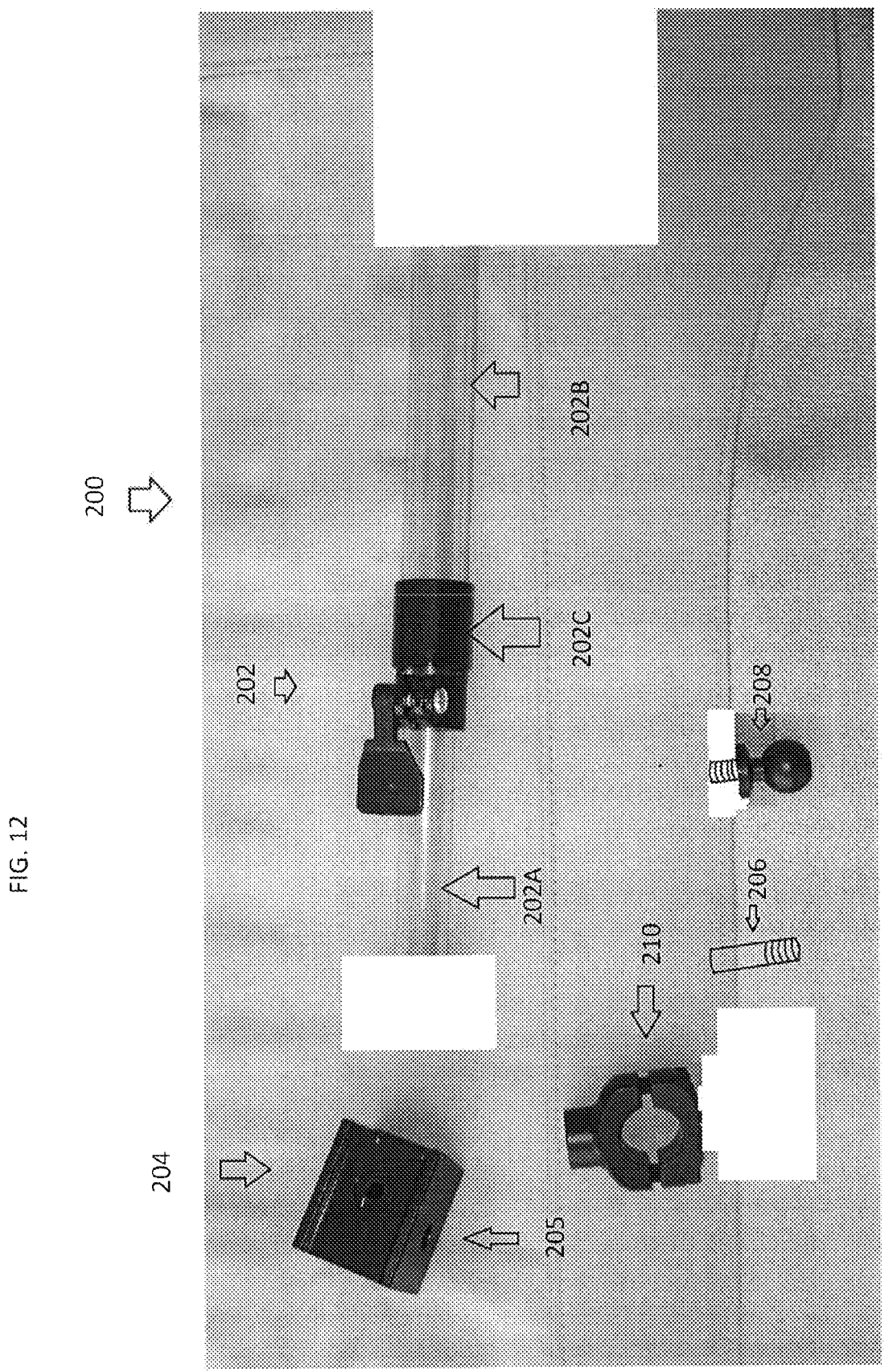
FIG. 12 is a view of the components of a system according to yet another exemplary embodiment of the invention.
Figure 13:
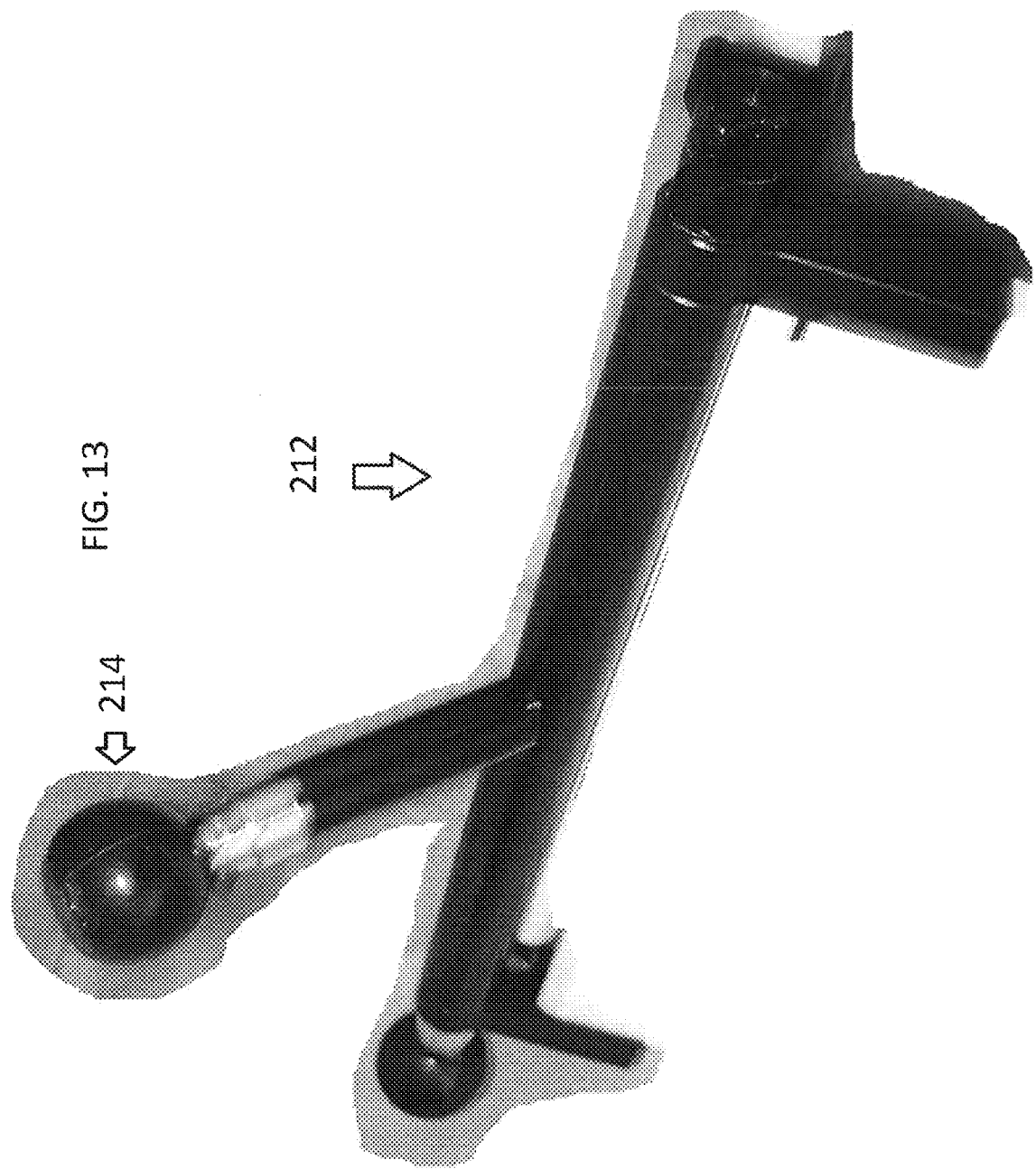
FIG. 13 is a view of a bracket that forms another part of the system of FIG. 12 coupled to a light therapy device.
Figure 14:
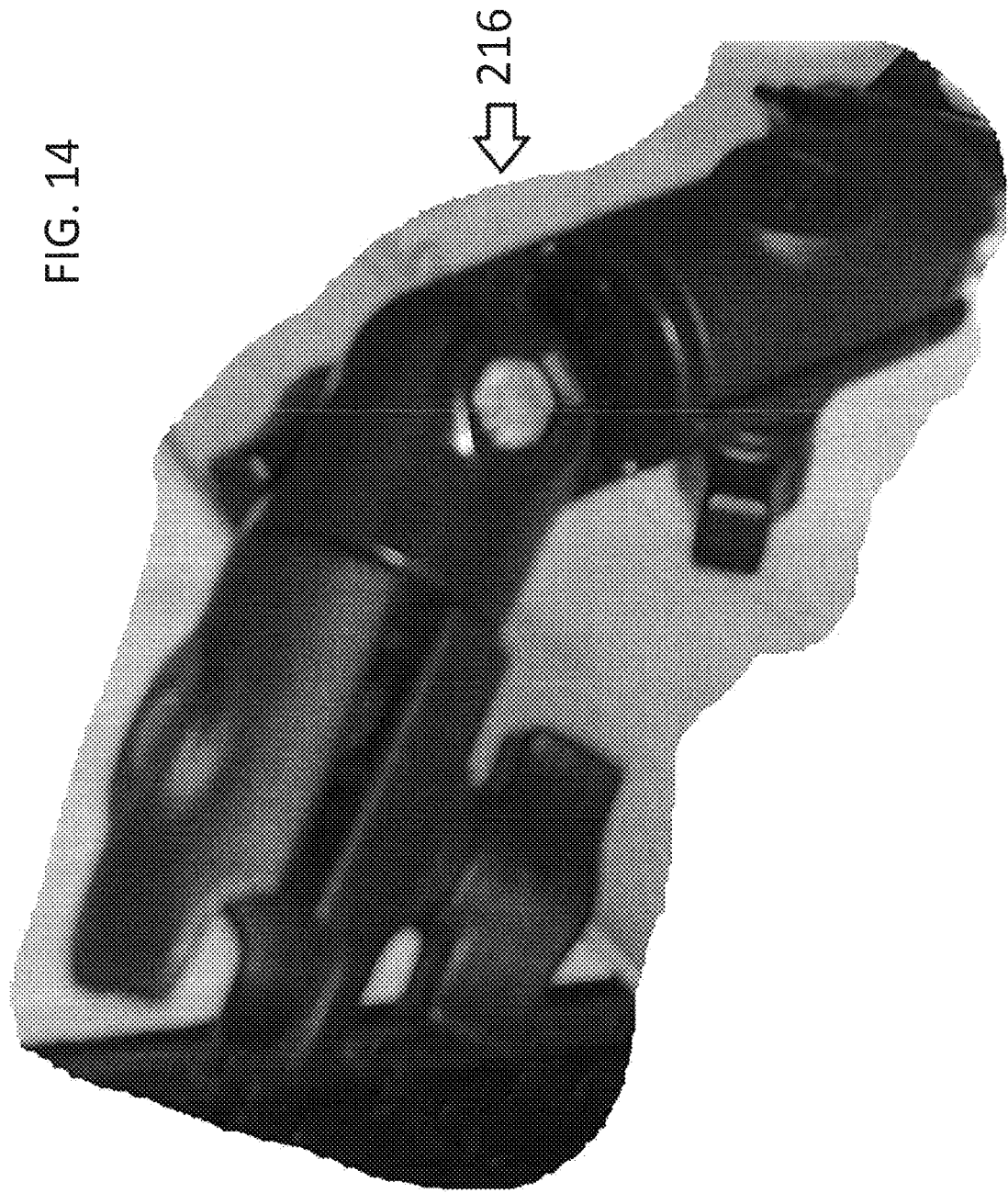
FIG. 14 is a view of a universal joint coupled to the structure of FIG. 13.

FIGS. 12 through 14 show the components of a system 200 which forms another aspect of the invention.

The system 200 is also for use with (i) a treatment bed having: one or more cushions for supporting a user in the supine or prone position; a bed frame supporting the one or more cushions; and a pair of grips, bolted on opposite sides of the bed frame, for assisting the user in movement to and from the supine and prone positions; and (ii) an energetic medical device having a waisted portion, all as shown in FIG. 1.

The system 200 comprises an extension tube 202, a mounting block 204, a threaded pin 206, a threaded knob 208, a clamp 210, a bracket 212 and a universal joint 216.

The extension tube 202 comprises a pair of tubes 202A, 202B telescopically mounted to one another and a clamp 202C adapted for securing the tubes 202A,202B against movement. The mounting block 204 has a plurality of threaded sockets 205. The threaded pin 206 has a threaded end adapted for threaded engagement in the socket 205 and an unthreaded end adapted for engagement in the socket 205. The clamp 210 is adapted to grasp either end of the extension tube 202 and also has a pair of threaded sockets 205. The knob 208 has a threaded end adapted for engagement in any of the threaded sockets 205 and a ball.

The bracket 212 is adapted to be secured to a therapy light and terminates in a ball 214 equal in size to that of the knob 208.

The universal joint 216 has a pair of ends each adapted to grasp a respective knob or ball.

Figure 15:
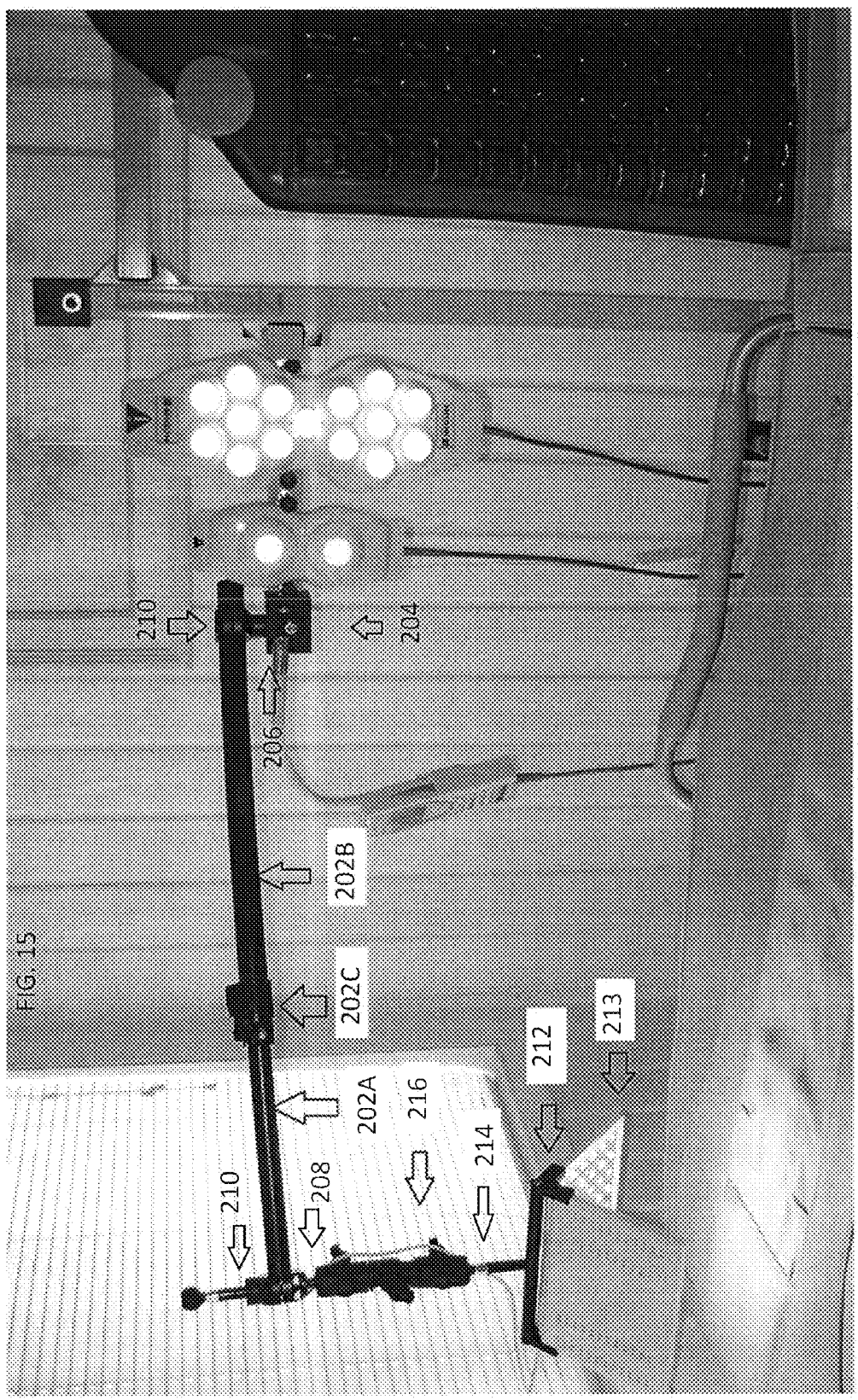
FIG. 15 is a view of the system of FIGS. 12 through 14 in use.

The system 200 is shown in use in FIG. 15. Here: a mounting block 204 will be seen secured to the end of a horizontal arm; one of the pins 206 has the unthreaded disposed in the mounting block 204 and another threaded end coupled to a clamp 210 to allow for rotational movement of the clamp 210; the clamp 210 is disposed in gripping relation to one end of an extension tube 202; a further clamp 210 is disposed at the other end of the extension tube 202; a threaded knob 208 is disposed in threaded relation in the further clamp 210; the universal joint 216 grasps the ball of threaded knob 208; the ball of the therapy light bracket is grasped by the other end of the universal joint 216, all such that the therapy light 213 is disposed over the bed.

Figure 16:
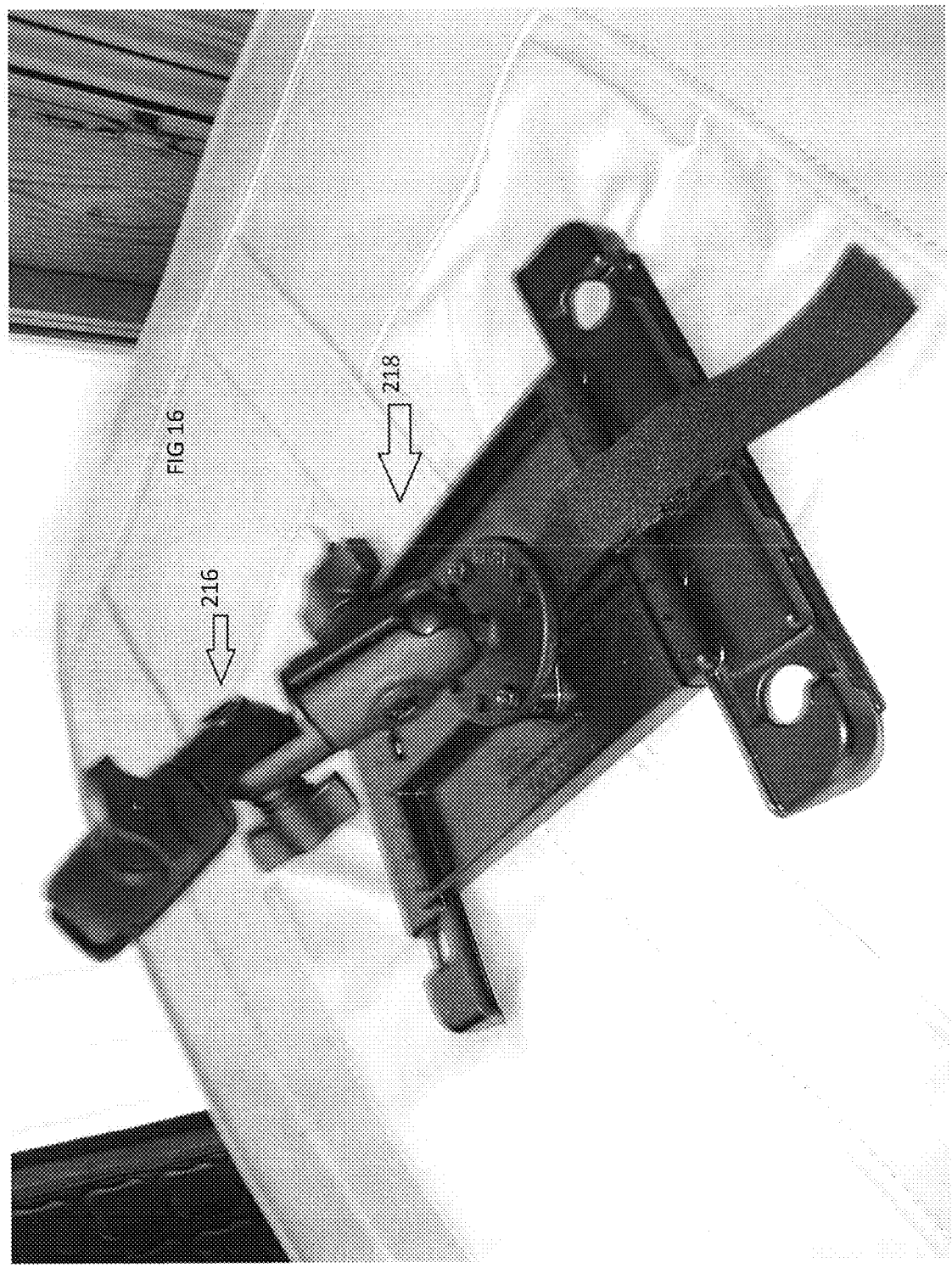
FIG. 16 is a view similar to FIG. 14 showing a tablet bracket coupled to the universal joint.

FIG. 16 shows a variation of the structure of FIG. 14; here, instead of a therapy light bracket 212, a tablet computer bracket is shown 218.

Figure 17:
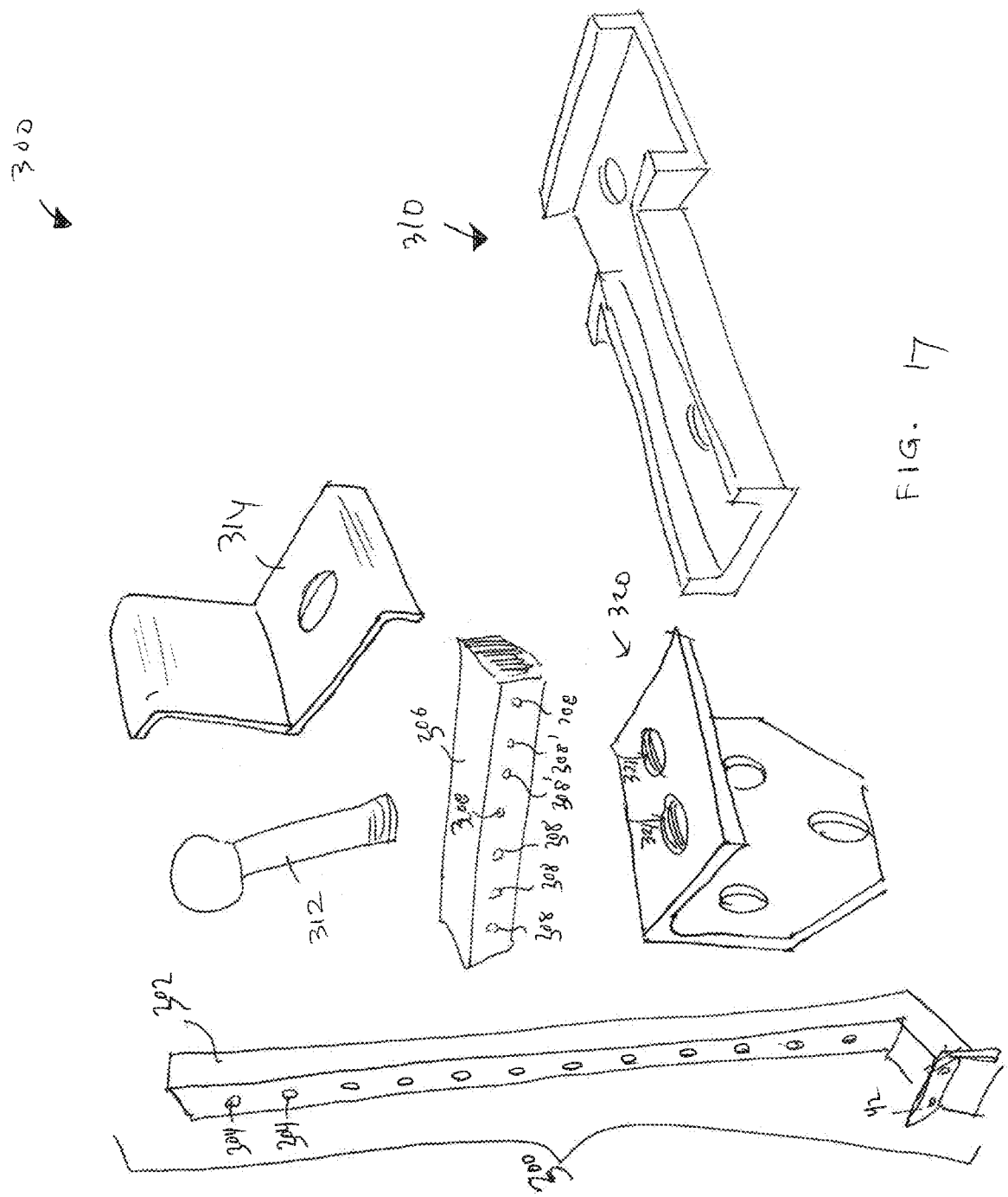
FIG. 17 is a view of components of another system that forms another aspect of the invention.

FIG. 17 shows the components of yet another system 300.

This system 300 comprises: a support frame 302 in the form of a square tube including a plurality of threaded bores 304 defined therein and terminating in a bracket 42 similar to that of FIG. 2; a lateral 306 in the form of a square tube having a plurality of threaded bores 308, 308' defined therein, at least a pair of the bores 308', 308' being spaced apart the width of the waisted portion; a cruciform bracket 310; posts 312 engageable in the threaded bores; a hook 314; and a mounting bracket 320.

Figure 18:
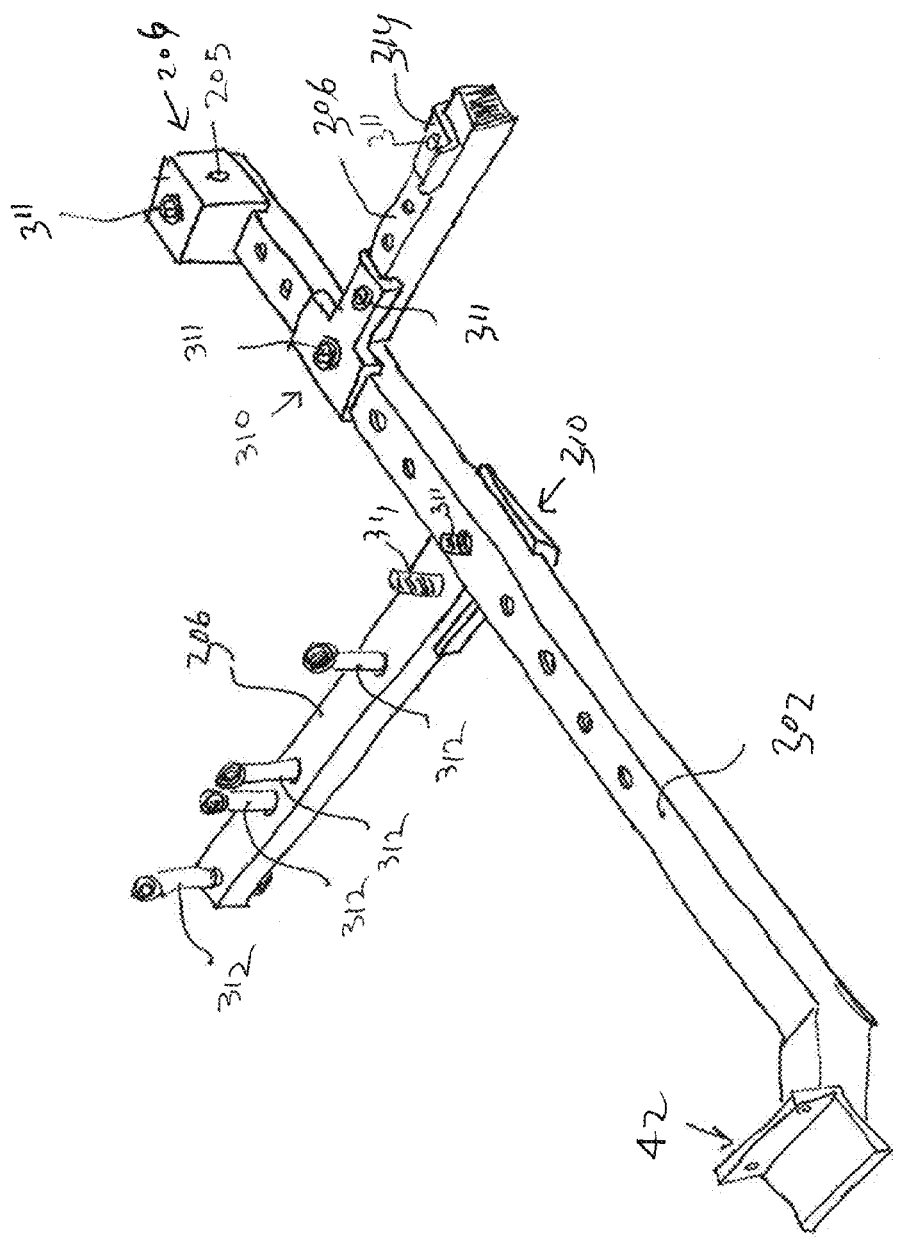
FIG. 18 is a view of an exemplary arrangement of the components of FIG. 17.

The support frame 302, lateral 306, posts 312, hook 314 and cruciform bracket 310 are shown in use in FIG. 18.

In this figure, these components will be seen to have been configured to assemble a structure similar in functionality to the structure of FIG. 2, i.e. which (i) can be secured to the bed frame in use, as shown in FIG. 3, such that one or more of the bolts bolting the support frame to the bed frame can form part of the bolts by which the grips are mounted to the bed frame, and (ii) can also be used as shown in FIG. 5, i.e. to support a treatment mat via the hook 214 and to support the energetic medical device via posts 212. More particularly, it will be seen that a pair of laterals 306 are each secured to the frame 302 via a respective cruciform bracket 310 [secured via bolts 311], and that the posts 312 are threaded into the sockets 308' to provide a rest for the energetic medical device.

The mounting block 204 is also shown in FIG. 18 and will be understood to be secured by a bolt 311 to a threaded socket 304 at the terminus of the upright for receiving, via the sockets 205, other fixtures such as lights, arms, etc.

Figure 19:
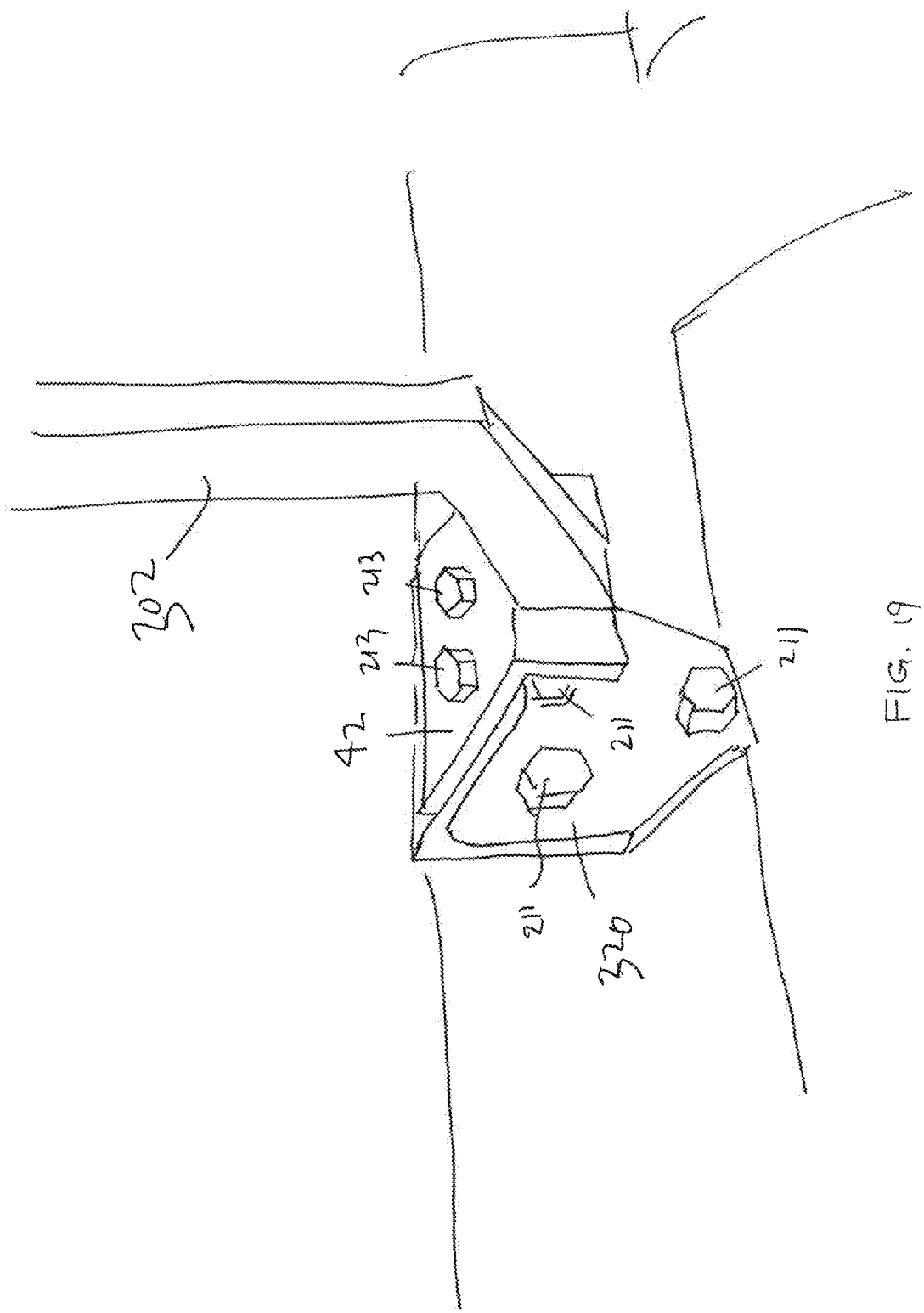
FIG. 19 is a view of a further exemplary arrangement of components of FIG. 17, in use.

The mounting bracket 320 is shown in FIG. 19 and will be seen to permit the support frame 302 to be mounted to the bed frame without use of the bolts by which the grips are mounted to the bed frame, more particularly, the bracket 320 is secured to the bed frame by bolts 211 which are unrelated to the grips, and the bracket 42 of the support frame is secured to the mounting bracket 320 by further bolts 213 which engage threaded sockets 321 in the bracket 320.

Figure 20:
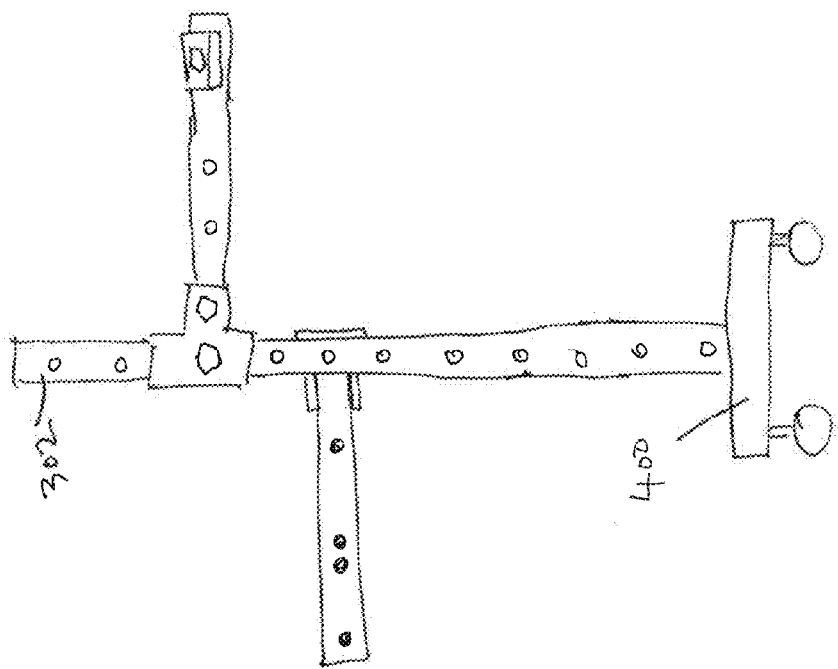
FIG. 20 is a view of another exemplary arrangement of the components of FIG. 17.

FIG. 20 shows yet another embodiment of the invention, wherein the support arm 302 is coupled to a rolling cart 400.

Figure 21A:
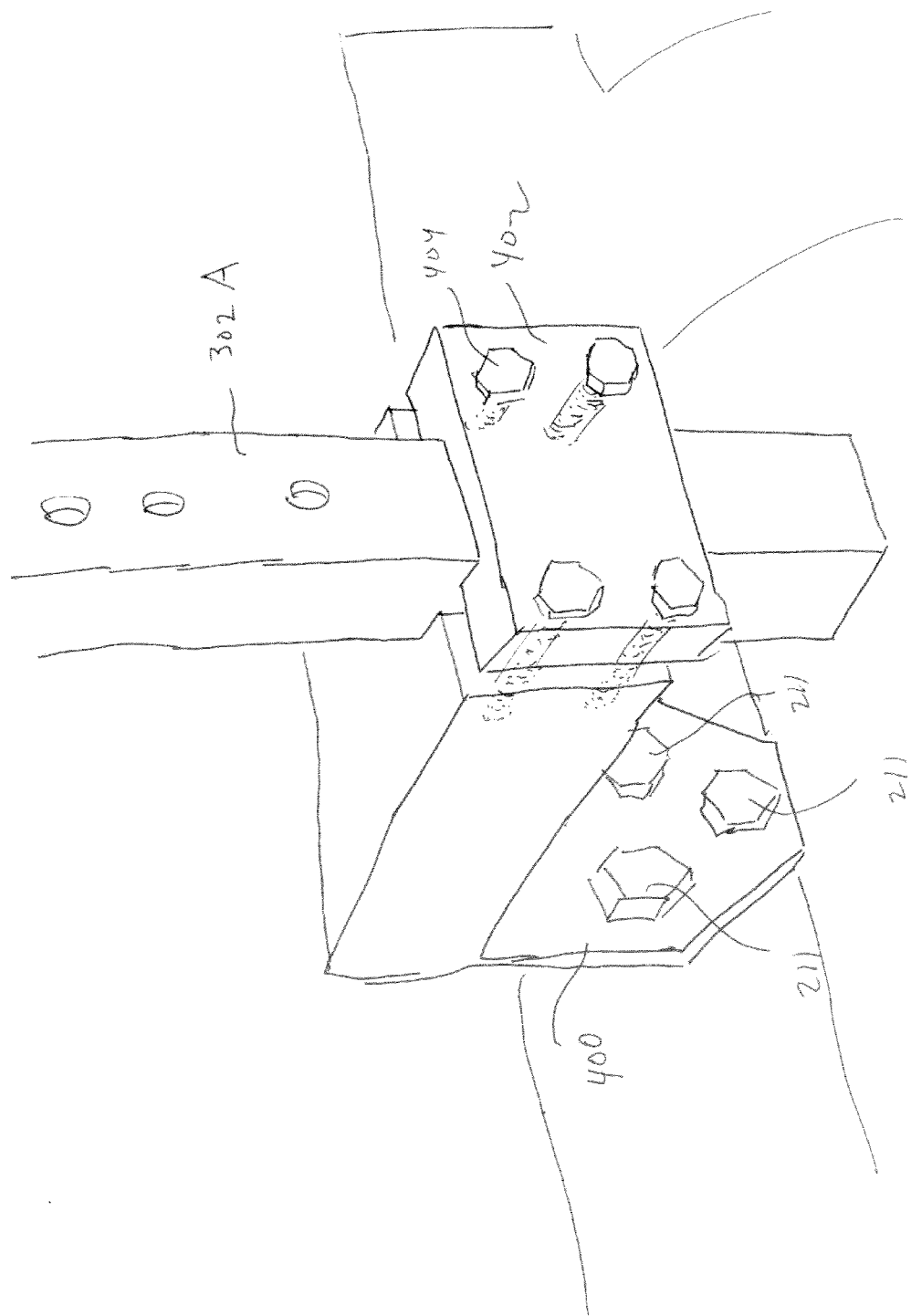
FIG. 21A is view of another embodiment of the structure of FIG. 19.

FIG. 21A shows another embodiment of the structure of FIG. 19 wherein a modified support arm 302 is secured to the treatment bed by means of a base bracket 400 that is secured to the treatment bed by bolts 211, and a cover bracket 402 that is secured to the base bracket by bolts 404 and grips around the modified support arm 302A.

FIG. 21B shows a variant of the structure of FIG. 21A, wherein a modified base bracket 406 terminates in an angle and is thereby adapted, for example, to be secured to square tubing.

FIG. 21C shows yet another variant, wherein a further modified base bracket 408 terminates in a flat plate.

Whereas in embodiments herein shown and described, the accessory bar is ostensibly an aftermarket type of product, it will be evident that the same could be added or combined to a treatment bed. Further, whereas a specific treatment bed is shown, it will be evident that the bed could, for example, be a vibrating bed, a traction device, etc.

Accordingly, the present invention should be understood as limited only by the accompanying claims, purposively construed.

The invention claimed is:

1. In combination:
   an energetic medical device having a waisted portion;
   a treatment bed having one or more cushions for supporting a user in the supine or prone position and a bed frame supporting the one or more cushions; and
   a support frame: bolted to the bed frame; and including a pair of horizontally extending posts adapted to receive therebetween the waisted portion of said energetic medical device to support the energetic medical device in elevated relation above and to one side of the treatment bed.

2. A system for use with:
   a treatment bed having: one or more cushions for supporting a user in the supine or prone position; a bed frame supporting the one or more cushions; and a pair of grips, bolted on opposite sides of the bed frame, for assisting the user in movement to and from the supine and prone positions; and
   an energetic medical device having a waisted portion
   the system comprising:
   a support frame adapted to be bolted to the frame to define an upright disposed to one side of the treatment bed, the upright having a plurality of bores defined therein;
   a lateral having a plurality of bores defined therein, at least a pair of the bores being spaced apart the width of the waisted portion;
   a cruciform bracket adapted to couple the lateral to the upright such that the bores present towards the treatment bed;
   posts engageable in the pair of bores such that, when the frame, lateral, cruciform bracket and posts are operatively assembly to the bed frame, the posts are adapted to support the energetic medical device in elevated relation above and to one side of the treatment bed.

3. A system according to claim 2, further comprising a hook adapted to be secured to the lateral to support a treatment mat.

4. A system according to claim 2, further comprising a mounting block adapted to be secured to any of the bores of the upright or the lateral.

5. A system according to claim 2,
   wherein the support frame is adapted to be secured to the bed frame in use such that one or more of the bolts bolting the support frame to the bed frame can form part of the bolts by which the grips are mounted to the bed frame;
   further comprising a bracket adapted to be secured to the bed frame and to support the upright without use of the bolts by which the grips are mounted to the bed frame.

* * * * *